United States Patent
Kolena et al.

(10) Patent No.: US 6,693,213 B1
(45) Date of Patent: Feb. 17, 2004

(54) METHOD OF PRODUCING ETHYL ACETATE AND AN EQUIPMENT FOR CARRYING OUT THIS METHOD

(75) Inventors: Jiri Kolena, Litvinov (CZ); Jaromir Lederer, Teplice (CZ); Pavel Morávek, Litvinov-Janov (CZ); Jiri Hanika, Praha (CZ); Quido Smejkal, Neratovice (CZ); David Skála, Ricany u Prahy (CZ)

(73) Assignee: Sulzer Chemtech AG, Winterthur (CH)

( * ) Notice: Subject to any disclaimer, the term of this patent is extended or adjusted under 35 U.S.C. 154(b) by 0 days.

(21) Appl. No.: 10/110,641
(22) PCT Filed: Oct. 11, 2000
(86) PCT No.: PCT/CZ00/00075
§ 371 (c)(1), (2), (4) Date: Apr. 12, 2002
(87) PCT Pub. No.: WO01/27065
PCT Pub. Date: Apr. 19, 2001

(30) Foreign Application Priority Data

Oct. 14, 1999 (CZ) .......................... 1999-3635

(51) Int. Cl.$^7$ ............................................. C07C 67/02
(52) U.S. Cl. ....................................................... 560/265
(58) Field of Search ......................................... 560/265

(56) References Cited

U.S. PATENT DOCUMENTS

| | | | |
|---|---|---|---|
| 4,481,146 A | * 11/1984 | Leupold et al. | 260/410.9 |
| 5,231,222 A | * 7/1993 | Papa et al. | 560/265 |
| 5,430,178 A | 7/1995 | Uhm et al. | |
| 6,028,215 A | 2/2000 | Bessling et al. | |

FOREIGN PATENT DOCUMENTS

WO    WO 99/48855    9/1999

OTHER PUBLICATIONS

Kirbaslar, E. I. et al, "Production of Ethyl Acetate by an Esterification Process" Chimica Acta Turcica, vol 25 pp. 37–41 (1997).*

Wagner, Jr. , Frank S. "Acetic Acid" monograph from Kirk–Othmer Encyclopedia of Chemical Technology (2002).*

* cited by examiner

*Primary Examiner*—Mark L. Berch
*Assistant Examiner*—Zachary C. Tucker
(74) *Attorney, Agent, or Firm*—Townsend and Townsend and Crew LLP

(57) ABSTRACT

The invention relates to a method of producing ethyl acetate by reaction of ethyl alcohol with acetic acid and/or acetic anhydride in the presence of a solid acidic catalyst accompanied by simultaneous distillation separation of reaction components, in which acetic acid or acetic anhydride or a mixture thereof and ethyl alcohol, respectively, are introduced separately in a molar ratio of 2:1 to 1:2.5 and in a defined quantity, per unit volume of catalyst, into a system separated into three zones, whereby, in the reaction zone, the reaction runs simultaneously with distillation separation of components, acetic acid feed is introduced into the reaction zone or above the zone and ethyl alcohol feed is introduced into the reaction zone or below this zone; in the upper separation zone, the volatile mixture is separated; thereafter, it is cooled to 5 to 70° C. and then separated into water and organic phases and the organic phase with a high ethyl acetate content is drawn off and partially returned as reflux flow into this system, whereby, the ratio of the starting components feed and the organic reflux flow is 1:1 to 1:20. This invention also relates to equipment for carrying out this method.

6 Claims, 1 Drawing Sheet ically active filling and a rectification and separation of reaction products take place simultaneously. The present invention relates also to equipment for carrying out this method.

METHOD OF PRODUCING ETHYL ACETATE AND AN EQUIPMENT FOR CARRYING OUT THIS METHOD

This application was filed under 35 U.S.C. 371, and is the U.S. National Stage of PCT/CZ00/00075, filed Oct. 11, 2000.

FIELD OF THE INVENTION

The present invention relates to a method of ethyl acetate synthesis by esterification of acetic acid with ethyl alcohol or by reaction of acetic anhydride with ethyl alcohol, which method uses catalytic distillation in a column, during which catalytic distillation a reaction on a catalytically active filling and a rectification and separation of reaction products take place simultaneously. The present invention relates also to equipment for carrying out this method.

BACKGROUND OF THE INVENTION

Ethyl acetate is prepared by reaction of ethyl alcohol and acetic acid, which reaction produces, apart from ethyl acetate, also water. Alternatively, ethyl acetate can be prepared by reaction of acetic anhydride with ethyl alcohol, during which reaction, apart from ethyl acetate, also acetic acid is produced, which acetic acid is further esterified by another portion of ethyl alcohol. The esterification is an equilibrium reaction and is accelerated by the presence of acid catalysts. For this purpose, predominantly mineral acids are used, preferably sulfuric acid or, as an advancement, solid acidic catalysts. Such acidic catalysts are mainly the acidic ion exchangers, or eventually zeolites, or the so-called solid superacids, and so on.

According to prior art methods, the reaction is usually carried out so that a nearly equilibrium composition of reaction mixture is obtained in a reactor, which composition depends on the starting molar ratio of reacting components. The so obtained mixture is rectified in a column, distilling out a mixture having a composition close to the ternary heterogenic azeotrope containing ethyl alcohol, ethyl acetate and water. Because the amount of water produced by this reaction is greater than the amount of water distilled in the form of the azeotrope, the superfluous water is withdrawn from the column boiler together with the unreacted acetic acid. The so obtained acetic acid has to be regenerated by another distillation. The following distillation separation of the organic phase of the ternary azeotrope so obtained, i.e. first of all, separation of the unreacted ethyl alcohol from ethyl acetate, is of course very demanding, considering that it is a substantially non-ideal mixture where ethyl alcohol and ethyl acetate form a binary azeotrope, and apart from that they form a ternary azeotrope with water having minimal boiling point. From the water phase, which was separated from the distillate of the first column, the dissolved ethyl acetate and ethyl alcohol are then distilled out by means of another distillation column, and this mixture of alcohol and acetate is then returned into the process. A complex method of separating the esterification reaction components is the main disadvantage of the prior art methods mentioned. In case of methods using the mineral acids as catalyst, significant environmental and corrosion problems are also observed.

In principle, it is also known to carry out the esterification of acetic acid by ethyl alcohol in a distillation column either in the absence of a catalyst (Chem. Eng. Technol. 1997, 20, 182) or by feeding a homogenous catalyst, i.e. a mineral acid, together with one of the reaction components (Chemia Stosowana 1989, 33, 509). Also, use of a batch column was disclosed, which column is filled with particles of an acidic ion exchanger, whereby such particles act both as a catalyst and as a column packing (Separation Science and Technology 1992, 27, 613). Of course, the rate of a non-catalytic esterification is too low to allow industrial use. The reactive distillation using a homogenous catalyst feed brings about the above-mentioned corrosion problems and environmental disadvantages. The distillation column packed with free particles of acidic catalyst is inapplicable in an industrial process because of high hydrodynamic resistance and poor separation efficiency.

Accordingly, it is an object of the present invention to eliminate the drawbacks of the prior art methods.

SUMMARY OF THE INVENTION

A method of producing ethyl acetate by reaction of ethyl alcohol with acetic acid and/or acetic anhydride according to the present invention consists in that, in the presence of a solid acidic catalyst and during simultaneous distillation separation of reaction components, acetic acid or acetic anhydride or their mixture and ethyl alcohol are introduced separately in a molar ratio of 2:1 to 1:2.5 and in a quantity, expressed as total flow rate, of 0.1 to 10 $h^{-1}$ of the introduced components, based on unit volume of catalyst, into the system, in which system the reaction and the distillation separation are carried out in three zones, whereby in a reaction zone the reaction runs simultaneously with the distillation separation of components having different boiling points, and in two separation zones only the distillation separation of components takes place, whereby water produced as a by-product of the reaction, forming a low-boiling azeotropic mixture with ethyl acetate, distills completely or partially from the system. Thereafter, the distillate is cooled to 5 to 70° C. and then water is separated from the ethyl acetate and other organic components of the distillate and is withdrawn from the system, whereas the organic components of the distillate, containing predominantly raw ethyl acetate, are partially returned back as reflux flow, whereby the feed stream of acetic acid and/or acetic anhydride and the ethyl alcohol feed are introduced into the system so that the acetic acid and/or acetic anhydride feeds are introduced into the reaction zone or above this zone into a place situated above the place of the ethyl alcohol feed, and the ethyl alcohol feed is introduced into the reaction zone or under this zone, whereby the ratio between the feed of the starting components into the column and the organic phase reflux flow into the column head is from 1:1 to 1:20, and the residual unreacted acetic acid that can contain a part of the water produced by chemical reaction and that was not separated in the form of distillate is separated as the higher boiling bottom component. As catalyst, an acidic ion exchanger can be used, for example a sulfonated styrene-divinylbenzene copolymer containing 1 to 25% by weight of divinylbenzene with acidity 1 to 10 meq($H^+$)/g. However, any other acidic ion exchanging resins, or for example acidic zeolites and other known acidic catalysts, can also be used.

A preferable embodiment of this method is operated maintaining the following characteristics: molar ratio of acetic acid to ethyl alcohol is 1:1 to 1:0.45, or that of acetic anhydride to ethyl alcohol is 1:2 to 1:1.5; feed flow rate of input components, based on unit volume of catalyst, is 0.5 to 5 $h^{-1}$; and ratio of the input components fed into the reaction to the organic phase reflux flow is 1:1 to 1:20. Instead of a pure acetic acid or acetic anhydride feed or their mixture, a partially reacted mixture of acetic acid or acetic anhydride and ethyl alcohol can be used, so that the feed stream containing acetic acid can also contain ethyl acetate and/or water and/or unreacted ethyl alcohol.

The method according to the present invention is carried out using equipment comprising a column consisting of three zones, whereby the reaction zone, placed in the middle part of the column, contains solid acidic catalyst fixed on distillation trays or, in a preferable embodiment, anchored in the known types of oriented packings with internal channel structure, where the catalyst is fixed between two layers of inert porous material forming the structure of the packing. The bottom separation zone and the top separation zone comprise inert poured packings, which are the structured oriented packings of known designs or distillation built-in parts. The acetic acid and/or acetic anhydride feed pipeline is connected into the upper part of the reaction zone or above this zone, the ethyl alcohol feed pipeline is introduced into the bottom part of the reaction zone or under this zone, the column bottom is provided with a boiler, the draw-off of the unreacted acetic acid is provided in the column boiler or in the column bottom, and the upper part of the column is terminated by a head, which head is provided with a withdrawal of distillate vapors into a condenser, whereby a condensed distillate pipeline is provided transferring the condensed distillate into a separator, whereby the separator is provided with a withdrawal pipeline for removal of the distillate water phase in the bottom part, an outlet pipeline for draining of the reflux flow, and an outlet pipeline for withdrawal of the distillate organic phase.

It is apparent from the above-specified summary of the invention that the method according to the present invention makes obtaining a higher than equilibrium, nearly 100% conversion, of the starting components to ethyl acetate and water, possible. Especially, if ethyl alcohol is supplied with a slight stoichiometric deficit into the system, ethyl alcohol is converted to ethyl acetate nearly completely, which ethyl acetate is then obtained in the form of an easily separable mixture with water. The separation zones fulfill the function of separating reaction products, i.e. ethyl acetate and water, from the starting components, i.e. acetic acid and ethyl alcohol, and returning of said starting components back into the reaction zone, whereby ethyl acetate is separated together with water as a distillate continually, and, after separation from the organic phase of this distillate, the water phase containing mainly ethyl acetate is separated from the system and the organic part of the distillate is partially returned to the column as back flow and is partially drawn off.

The starting materials, i.e. acetic acid or acetic anhydride and ethyl alcohol, can be fed into the reaction zone either in stoichiometric ratio or with molar excess of acetic acid and/or acetic anhydride to convert nearly all the ethyl alcohol. If the method according to the present invention is carried out at atmospheric pressure, the temperature mode of the column is stabilized so that the temperature in the column head reaches 70 to 74° C. Feed of the starting components into the column is carried out so that ethyl alcohol is introduced into a lower place of the column than the acetic acid and/or acetic anhydride feed. In a usual embodiment of this method, ethyl alcohol is fed under the catalytic zone or into its lower part. On the other hand, the feed containing acetic acid or acetic anhydride is fed above this zone or into its upper part.

Vapors passing away from the column head condense, producing a mixture, which mixture is cooled to 70 to 5° C. and then separated into water and organic phases, whereby a part of the organic phase containing primarily ethyl acetate is returned back into the column head as back flow and part of it is drawn off. A specific feature of the method according to this invention is low ethyl alcohol content in the distillate, which content is lower than what would correspond to the concentration in the ethyl acetate-ethanol-water ternary azeotrope. This fact significantly facilitates final purification of the distillate product to one of commercial purity by a not very demanding subsequent distillation. The water phase containing a quantity of dissolved ethyl acetate and eventually ethyl alcohol is drawn off. The dissolved ester and alcohol can be stripped off from this phase and both components can be returned back into the process. The excessive acetic acid is drawn off from the column boiler continually. The method according to the present invention makes it possible to separate all water produced by chemical reaction in the form of distillate or to withdraw a part of this water from the system as the bottom product together with the unreacted residual acetic acid.

BRIEF DESCRIPTION OF THE DRAWINGS

The attached

DETAILED DESCRIPTION OF THE INVENTION

Figure 1:
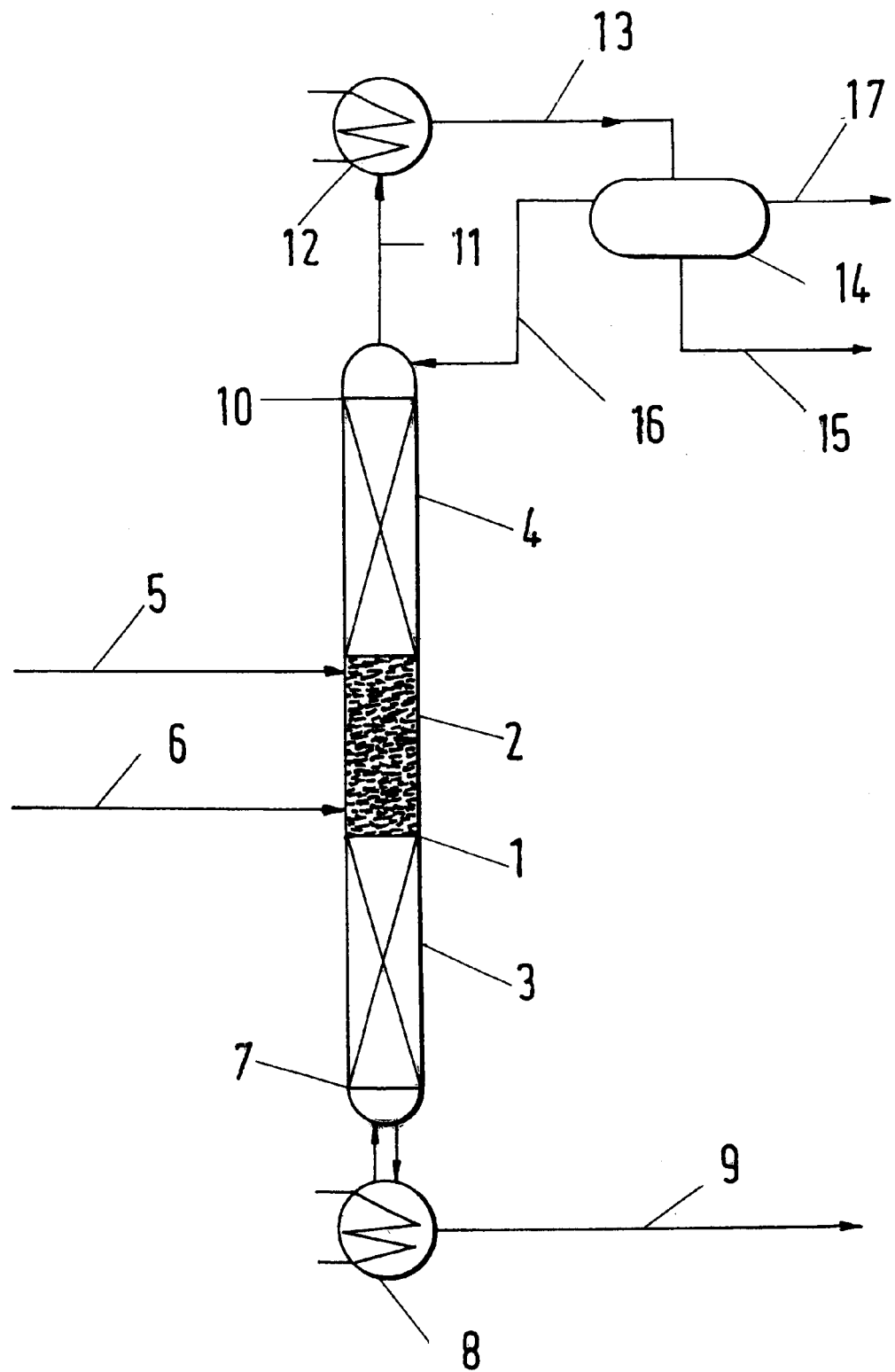
FIG. 1 shows a schematic drawing of equipment for carrying out the method according to the present invention.

The equipment according to FIG. 1 comprises a column 1 consisting of three zones, whereby the reaction zone 2 placed in the middle part of column 1 contains solid catalyst, and the bottom separation zone 3 and the upper separation zone 4 contain oriented packings, inert poured packings or distillation built-in parts. The acetic acid and/or acetic anhydride feed pipeline 5 is situated in the upper part of the reaction zone 2 or above this zone, and the ethyl alcohol feed pipeline 6 is brought into the bottom part of the reaction zone 2 or under this zone. The bottom part of the column 1 is terminated by a column bottom 7, which column bottom 7 is provided with a boiler 8. An unreacted acetic acid withdrawal pipeline 9 is connected to this boiler 8. The upper part of this column 1 is terminated by a column head 10. This column head 10 is provided with a distillate vapors withdrawal pipeline 11 passing said vapors into a condenser 12. A condensed distillate withdrawal pipeline 13 interconnects the condenser 12 with a separator 14. The bottom part of this separator 14 is provided with a distillate water phase withdrawal pipeline 15; the upper part of the separator 14 is provided with a reflux flow pipeline 16 and a non-refluxed distillate organic phase, i.e. ethyl acetate, withdrawal pipeline 17.

The method according to the present invention is carried out in the above-described equipment so that the feed of acetic acid and/or acetic anhydride or of their mixture with ethyl acetate and/or water and/or ethyl alcohol is fed through the pipeline 5 into the bottom part of the upper separation zone 4 or into the upper part of the reaction zone 2, while the ethyl alcohol feed is brought through the pipeline 6 into the upper part of the bottom separation zone 3 or into the bottom part of the reaction zone 2, whereby distillate vapors containing water, ethyl acetate and residues of unreacted ethyl alcohol are drawn off from the column head 10, pass into the condenser 12 and are then transferred further from this condenser 12 in the form of condensed distillate into the separator 14, where the distillate water phase is separated from the distillate organic components. The organic components are then returned from the separator 14 back into the column 1.

EXAMPLES OF INVENTION EMBODIMENTS

Example 1

FIG. 1 shows a schematic drawing of equipment according to the present invention. An atmospheric continually operated catalytic distillation column 1 was divided into three zones. The middle part of the column 1 forms the reaction zone 2. Under the reaction zone 2, a bottom separation zone 3 is provided and above the reaction zone 2 an upper separation zone 4 is provided. A boiler 8 is connected to the column bottom 7. A condenser 12 is connected to the column head 10. A separator 14 is connected to the condenser 12.

The reaction zone 2 was packed with catalytically active packing containing 33 g of acidic ion exchanger. Poured fillings were placed both in the bottom separation zone 3 and the upper separation zone 4 (Berl® saddles of diameter 4 mm). The length of the separation zones 3 and 4 was 0.5 m.

The method of production consisted in that ethyl alcohol feed was brought by pipeline 6 into the bottom separation zone 3 and the acetic acid feed was brought by pipeline 5 into the upper separation zone 4. The flow rate of both above-mentioned starting materials was 0.25 mol/h. Distillate vapors were drawn off by pipeline 11 from the column head 10 and transferred into the condenser 12. The condensed distillate was brought by pipeline 13 from the condenser 12 and passed into the separator 14. The produced reaction water was drawn off with flow rate 4.2 g/h in the form of a distillate water phase through pipeline 15 from the separator 14, the organic phase of distilled azeotrope was drawn off with a flow rate of 21 g/h as raw ethyl acetate, and the greater part of this organic phase was returned as reflux flow by pipeline 16 into the column 1. The unreacted acetic acid was drawn off with a flow rate of 1.2 g/h by the withdrawal pipeline 9 from the boiler 8 so that a constant level was maintained in this boiler 8. Reaction conversion in this configuration was 92%.

Example 2

Ethyl acetate synthesis was carried out using identical conditions as in Example 1 with the exception that the starting component was acetic anhydride instead of acetic acid, which acetic anhydride reacted in the pre-reactor in equimolar ratio with ethyl alcohol, producing acetic acid and ethyl acetate. The reaction mixture was then fed to the column 1 instead of acetic acid. The selected total molar ratio of ethyl alcohol to acetic anhydride was 1.52. Using a reflux ratio of 1:6, the output of the apparatus was 0.46 mol/h of raw ethyl acetate with purity 91.4% by weight. Apart from ethyl acetate the product contained only 5.2% by weight of water and 3.4% by weight of ethyl alcohol. The output flow rate of the separated water phase in the separator 14 was 3.9 ml/h.

Example 3

Ethyl alcohol esterification by acetic acid was carried out using an apparatus comprising a boiler 8 having a volume of 50 liters, and a column 1 provided with a condenser 12 and with a separator 14. The catalytic distillation column 1 consisted of a reaction zone 2 packed with catalytically active packing KATAPAK® S with 1.07 kg of acidic ion exchanger in H⁺form. The bottom separation zone 3 and the upper separation zone 4 were filled with oriented packing of efficiency 12 (the bottom separation zone), i.e. 20 theoretical plates. Acetic acid was fed in a quantity of 0.73 kg/h through the pipeline 5 into the reaction zone 2 and ethyl alcohol was fed in a quantity of 0.41 kg/h through the pipeline 6 to the upper boundary of the bottom separation zone 3. Water produced by this reaction was drained off from the separator 14 by the pipeline 15, the organic phase was refluxed by the pipeline 16 into the column 1, and a part of the organic phase (0.86 kg/h) was drawn off as raw ethyl acetate through the pipeline 17. By drawing off the unreacted acetic acid through the pipeline 9, constant retention in the boiler 8 was maintained. Apart from ethyl acetate the product contained 0.003% by weight of acetic acid, 1.4% by weight of ethyl alcohol and 1.43% by weight of water.

Example 4

The equipment and method were the same as in Example 3 with the difference that the feed stream 5 contained 66.6% by weight of acetic acid, 0.8% by weight of ethyl alcohol, 25.4% by weight of ethyl acetate and 7.2% by weight of water. The feed rate was 0.843 kg/h. The feed of this composition was obtained by the previous partial reacting of an acetic acid-ethyl alcohol mixture by passage through a reactor of conventional design, filled with acid ion exchanger. Ethyl acetate was then drawn off from the separator 14 at a flow rate of 0.84 kg/h. The ethyl acetate of purity 96.1% by weight contained 2.6% by weight of water and 0.5% by weight of ethyl alcohol. No presence of acetic acid in the product was found by the gas chromatography method.

Industrial Use

The present invention will find use in the chemical industry. The product obtained is suitable mainly as a solvent in the production and use of coating materials and as an extraction agent in pharmacy and biotechnology.

What is claimed is:

1. A method of producing ethyl acetate by reaction of ethyl alcohol with acetic acid and/or acetic anhydride in the presence of a solid acidic catalyst accompanied by simultaneous distillation separation of reaction components, characterized in that acetic acid or acetic anhydride or a mixture thereof, and ethyl alcohol, respectively, are introduced separately in a molar ratio of 2:1 to 1:2.5 and in a quantity, expressed as a total flow rate of 0.1 to 10 $h^{-1}$ of the introduced components, per unit volume of catalyst, into a system, in which system the reaction and the distillation separation are carried out in three zones, whereby, in the reaction zone, which is centrally located between an upper separation zone and a lower separation zone, the reaction runs simultaneously with the distillation separation of components having different boiling points, while separation of components takes place in said upper and lower separation zones, whereby water produced as a by-product of the reaction forms a low-boiling azeotropic mixture with ethyl acetate, and distills completely or partially from the system; the distillate is thereafter cooled to 5 to 70° C.; water is then separated from the ethyl acetate and other organic components of the distillate and is withdrawn from the system, the organic components of the distillate containing predominantly raw ethyl acetate, being partially returned back as reflux flow and partially withdrawn, whereby the ethyl alcohol feed and the acetic acid or acetic anhydride feed or that of their mixture are introduced into the system so that the acetic acid feed and/or the acetic anhydride feed and/or that of their mixture are introduced into the reaction zone or above this zone into a place situated above the place of introduction of the ethyl alcohol feed, and the ethyl alcohol feed is introduced into the reaction zone or under this zone, whereby the ratio between the feed of the starting components into the column and the organic phase reflux is 1:1 to 1:20, and the unreacted acetic acid is separated as the higher boiling bottom component.

2. A method according to claim 1 characterized in that said starting acetic acid or said acetic anhydride or their mixture contain also ethyl acetate and/or water and/or ethyl alcohol.

3. A method according to claim 1 characterized in that said acetic acid or said acetic anhydride or their mixture are introduced into the system in a molar ratio of 1:1 to 1:0.45 to said ethyl alcohol.

4. A method according to claim 1 characterized in that the total flow rate of said introduced starting components based on a unit volume of catalyst is 0.5 to 5 $h^{-1}$.

5. A method according to claim 1 characterized in that the ratio between feed of said introduced starting components into the reaction and reflux flow of said organic phase back into the reaction is 1:1 to 1:20.

6. A method according to claim 1 characterized in that the said unreacted acetic acid, separated from the system as the higher boiling bottom component, contains a part of the water produced by chemical reaction.

* * * * *